Oct. 24, 1950 H. C. SWIM Plant Pat. 984
ROSE PLANT
Filed Nov. 7, 1949
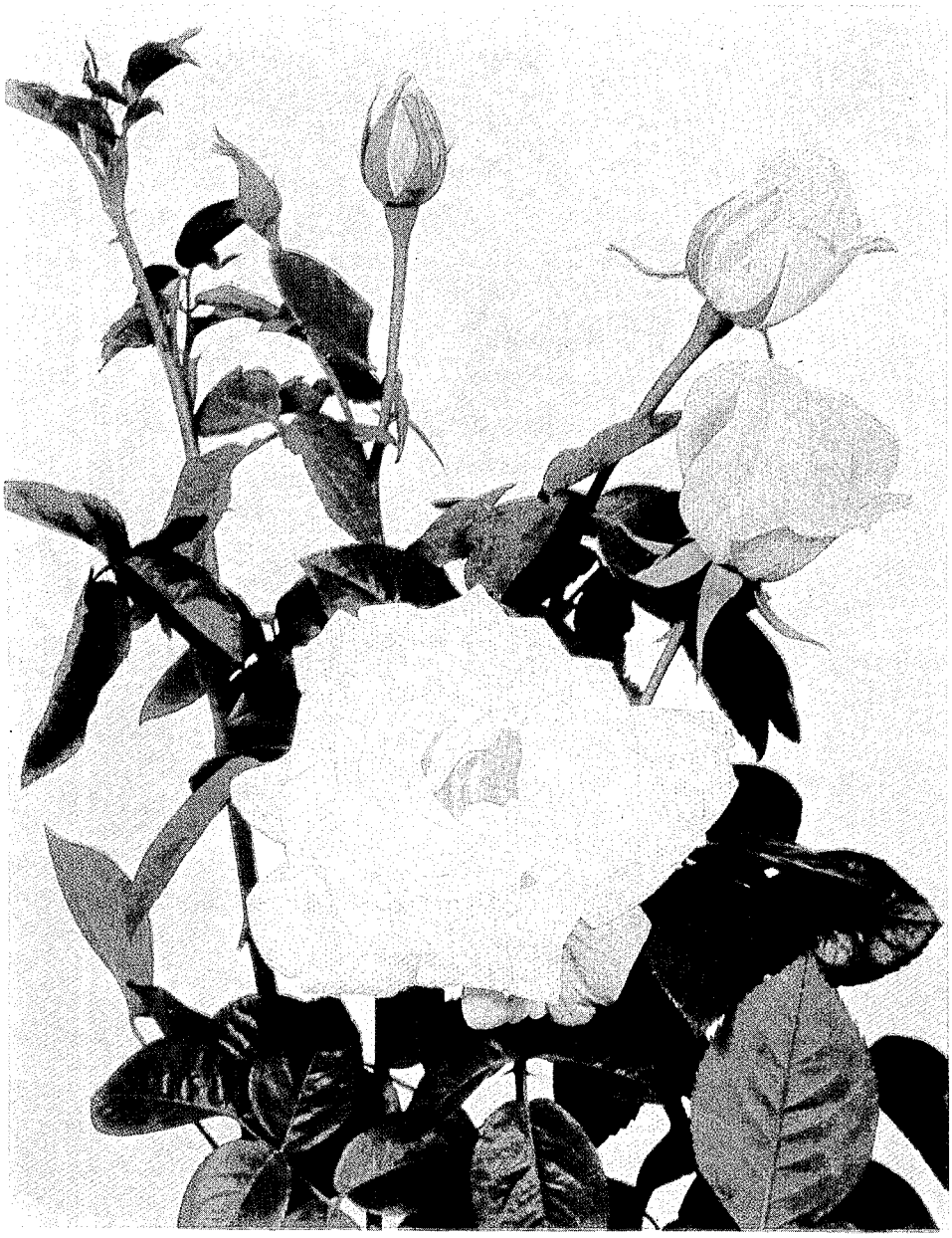
Inventor
H. C. Swim
By Robb & Robb
Attorneys Patented Oct. 24, 1950

Plant Pat. 984

UNITED STATES PATENT OFFICE

984

ROSE PLANT

Herbert C. Swim, Ontario, Calif., assignor, by mesne assignments, to Paramount Nurseries, West Grove, Pa., a corporation of Pennsylvania Application November 7, 1949, Serial No. 125,853

1 Claim. (Cl. 47—61)

The present invention relates to a new and distinct variety of rose plant, produced by the crossing of two well-known commercial roses, hereinafter referred to, and having as a definite objective the creation of a rose variety with improved characteristics in outdoor grown plants used for cut flowers and garden decoration.

This new variety is characterized as to novelty by the following distinctions:

(1) Its very vigorous growing habit, thereby producing a plant adequately clothed with heavy, medium sized glaucous leaves.

(2) Its production of buds and flowers of a color substantially as illustrated in the accompanying drawing and more specifically described hereinafter, the buds being characteristically medium to long pointed and the open flowers characterized by petals that reflex along both margins adjacent to the apex, giving the aging flower much the same appearance as a "Cactus Dahlia."

(3) Its markedly above-average resistance to mildew and black spot.

This combination of characteristics, to the best of my knowledge, mark this new variety as distinct from any variety now known to commerce.

Speaking with reference to its parents, it differs from its seed parent in the following way:

(*a*) While the color of this new variety is more generally characterized by the colors that are commonly called orange, salmon, and buff in various combinations and intensities, the flowers of the seed parent are typically found in various shades of red or deep pink. Although there is a slight amount of red pigment in the bud of this new variety, it definitely is not dominant as it is in "Charlotte Armstrong."

(*b*) The shape of both the buds and the open flowers of this new variety are distinct from those of "Charlotte Armstrong" since the buds are medium to long pointed and have very little reflex at the tip, whereas those of "Charlotte Armstrong" are very long pointed and distinctly reflex at the tip. The "Cactus Dahlia" appearance of the aging flowers of this new variety is distinct from the less extreme and more flat open flowers of "Charlotte Armstrong."

This new variety is distinct from its pollen parent in the following way:

(*a*) Whereas "Glowing Sunset" is moderate in growth, this new variety is very vigorous.

(*b*) Whereas the flowers of "Glowing Sunset" are predominated by orange pigment, the flowers of this new variety are dominantly salmon.

(*c*) Whereas "Glowing Sunset" is characterized by buds of urn shape, this new variety produces buds that are medium to long pointed without an appreciable reflex at the tip.

(*d*) Whereas the open flowers of "Glowing Sunset" are characteristically flat, the flowers of this new variety are typified by a form that is often described as "Cactus Dahlia."

(*e*) The foliage of "Glowing Sunset" is average or normal in quantity, whereas the foliage of this new variety is abundant.

Asexual reproduction of this new variety shows the foregoing characteristics come true to form and are established.

In the drawings are shown specimens of the new variety at different stages of development of both the blossoms and the foliage.

This new variety was asexually reproduced at Ontario, California, by budding.

The following is a detailed description of the new variety, all reference to color being in accordance with the Robert F. Wilson Horticultural Colour Chart (1938), except where indicated to be in accordance with Ridgway's Color Standards and Nomenclature:

Type: Bush; outdoor; seedling; for cut flowers and garden decoration.
Class: Hybrid tea.
Breeding: Seedling.
*Seed parent.*—"Charlotte Armstrong" (Pl. Pat. No. 455).
*Pollen parent.*—"Glowing Sunset" (Pl. Pat. No. 104).
Propagation: Holds its distinguishing characteristics through succeeding propagations.

*Flower*

Locality where grown: Ontario, California.
Flowers borne: Usually singly, sometimes two to three or more to stem; in irregular cluster; on normal medium to long stems.
Quantity of bloom: Abundant; outdoors.
Continuity: Intermittent during growing season.
Fragrance: Slight to moderate; tea.
Bud:
*Peduncle.*—Average length; average caliper; erect; moderately smooth except for a few gland-tipped cilia. Color—Parrot Green, Plate VI (Ridgway).
*Before calyx breaks.*—Size—medium. Form—medium length; ovoid; with foliaceous appendages and bloom on the surface of the bud; usually with slender much-cut bristle-like foliaceous parts extending beyond the tip of the bud equal to one-half or more of its length.

*As calyx breaks.*—Color—lighter portions are Geranium Lake, Plate 20/1, page 20; portions exposed to the sun are Cardinal Red, Plate 822/2, page 168.

*Sepals.*—Inner surface with fine tomentum; margins lined with stipitate glands and tomentum except where margins are covered by adjacent sepals, then margins are lined only with tomentum.

*As first petal opens.*—Size—large. Form—medium length to long; pointed. Color—outside—basal region of petal is Empire Yellow, Plate 603, page 66. Basic color for the rest of the petal outer surface is Shell Pink, Plate 516, page 135. Where petal was first exposed by spreading apart of the sepals, the color varies between Rose Opal, Plate 022, page 110, and China Rose, Plate 024, page 111, with the remaining portions of the petal shaded with the latter colors in varying degrees, probably depending upon the length of exposure; inside—basal region of petal is Empire Yellow, Plate 603, page 66. Basic color for the rest of the petal inner surface is French Rose, Plate 520/2, page 136. Darker shadings on this side of the petal correspond roughly to the deeper portions of the outside petal surface. These deeper shadings vary between Porcelain Rose, Plate 620, page 147, and the base color of French Rose, Plate 520/2, page 136.

*Opening.*—Opens up well; is not retarded from opening by cold, hot or dry weather.

Bloom: Size, when fully open—large; 4 inches to 4¾ inches.

*Petalage.*—Double; from 25 to 35 petals, plus 3 to 12 petaloids; arranged irregularly.

*Form.*—High centered at first; becoming flat to loosely globular; petals lateral margin at first loosely rolled outward; becoming later, at maturity, very much more tightly rolled outward.

Petals:

*Texture.*—Medium thin; with inside slightly velvety and outside slightly shiny to velvety.

*Shape.*—Outside—broadly cuneate with apex slightly rounded; usually with 1 to 2 notches. Intermediate—cuneate with apex rounded, usually with no notches. Inside—narrowly cuneate with apex rounded with usually no notches.

*Color.*—Colors may be modified by being blotched, shaded, washed or streaked with other colors.

This description of a newly opened flower was made from a rose grown outdoors in the month of September, at Ontario, California:

*Color.*—*Outside petal*—Outside surface: Aureolin, Plate 3, page 3, at petal base, gradually becoming Dawn Pink, Plate 523/1, page 137; this base color is streaked and washed with varying amounts of Carmine Rose, Plate 621/1, page 75, being blotched with colors between Cherry, Plate 722, page 157, and Rose Red, Plate 724, page 158. This blotch is that area of petal first exposed by the spreading sepals; inside surface: Aureolin, Plate 3, page 3, at petal base, gradually becoming Crimson, Plate 22/3, page 22, being washed and streaked with varying amounts of Tyrian Rose, Plate 24/2, page 24. *Intermediate petal*—outside surface; Aureolin, Plate 3/1, page 3, at base gradually becoming Shell Pink, Plate 516/1, page 135, with extremities fading to near Egyptian Buff, Plate 407/3, page 122; inside surface: Aureolin, Plate 3/1, page 3, at base gradually becoming shaded with Shell Pink, Plate 516/2, page 135. Base color and extremities are Egyptian Buff, Plate 407/3, page 122. *Inner petal*—outside surface: Aureolin, Plate 3/1, page 3, at base with remaining portions of Shell Pink, Plate 516/1, page 135; inside surface: Aureolin, Plate 3/1, page 3, at base with remaining portions Begonia, Plate 619/2, page 146.

This description was made from a rose that was open for three days outdoors in the month of September, at Ontario, California:

*Color.*—*Outside petal*—outside surface: Mimosa Yellow, Plate 602/1, page 143, at petal base, gradually mixing with a base color for rest of petal varying from Rhodamine Pink, Plate 527/2, page 138, to Camellia Rose, Plate 622/2, page 148. This base color is washed and streaked with various amounts of Fuchsine Pink, Plate 627/1, page 78; inside surface: Mimosa Yellow, Plate 602/1, page 143, at petal base. The rest of the inside surface is of colors varying between Rhodamine Pink, Plate 527/1, page 138, and Persian Rose, Plate 628/1, page 149. This variation in color is greater between petals than within one petal. *Inside petal*—outside surface: Mimosa Yellow, Plate 602, page 143, at petal base, shading upward into the Dawn Pink, Plate 523/2, page 137, base color, innermost petals and petaloids are washed with varying amounts of Rhodamine Pink, Plate 527/2, page 138; inside surface: Mimosa Yellow, Plate 602, page 143, at petal base shading upward into the Dawn Pink, Plate 523/2, page 137.

*General color effects.*—Newly opened flower—variable but near Shell Pink, Plate 516/1, page 135. Three days open—near Rose Pink, Plate 427/2, page 126.

*Behavior.*—Drop off cleanly except for petaloids; fading to Rose Pink, Plate 427/3, page 126.

*Flower longevity.*—On bush in garden—3 to 4 days in October. Cut roses grown outdoors kept at liviing room temperatures—2 to 3 days in October.

*Reproductive organs*

Stamens: Few to average number; arranged irregularly about pistils, a few mixed with petaloids.

Filaments: Medium length to long; 5 to 15 mm. in length; most with anthers. Color—near Saturn Red, Plate 13/2, page 13, at base changing to Cadmium Orange, Plate 8/3, page 8, at anther.

Anthers: Medium size; all open at once approximately. Color—central portions—near Amber Yellow, Plate 505/3, page 132. Margins—Lemon Yellow, Plate 4/2, page 4.

Pollen: Moderately abundant. Color—near Lemon Yellow, Plate 4/2, page 4.

Pistils: Many; approximately 90 in number.

Styles: Uneven; average length; average caliper; loosely bunched. Color—Blood Red, Plate Plate 820/3, page 166.

Stigma: Grayish-white, somewhat translucent.

5

Ovaries: Usually all enclosed in calyx.

Hips: Average to large size; globular; smooth; walls medium thick, fleshy. Color—three-fourths mature hip, Grape Green, Plate XLI (Ridgway).

Sepals: From newly opened flower—permanent; medium length; spear-shaped; spreading. Color—inside: Light Turtle Green, Plate XXXII (Ridgway); outside: Between Courge Green, Plates XVII (Ridgway) and Biscay Green, Plate XVII (Ridgway).

Seeds: Average number; medium size; 4 to 12 in number.

Foliage:

*Leaves.*—Compound of usually 5 to 7 leaflets; normal to abundant; medium size; moderately heavy; glaucous.

*Leaflets.*—Shape—ovate with apex acute; base round; margin doubly serrate. Color—mature—upper surface: near Parsley Green, Plate 00962, page 193; under surface: near Mytho Green, Plate XLI (Ridgway). Young—upper surface: Light Cress Green, Plate XXXI (Ridgway), lightly overlaid with Vandyke Red, Plate XIII (Ridgway); under surface: near Deep Chrysolite Green, Plate XXXI (Ridgway), somewhat overlaid with Vandyke Red, Plate XIII (Ridgway).

*Rachis.*—Average size. Upper side—grooved with many stipitate glands on edges. Under side—extremely prickly and with stipitate glands.

*Stipules.*—Medium length; narrow to medium width; medium length to long points, turning out at an angle of more than 45°.

*Disease.*—More than average resistant to mildew and black spot.

6

Growth:

*Habit.*—Bushy; moderately branched.

*Growth.*—Very vigorous.

*Canes.*—Medium caliper

*Main Stems.*—Color—Biscay Green, Plate XVII (Ridgway). *Large prickles*—several; medium length to long; hooked slightly downward with medium-length moderately narrow base. Color—Russet, Plate XV (Ridgway). *Small prickles*—few. Color—Russet, Plate XV (Ridgway). *Hairs*—none.

*Branches.*—Color—Chromium Green, Plate XXXII (Ridgway). *Large prickles*—several; medium length to long; hooked slightly downward. Color—Citron Yellow, Plate XVI (Ridgway). *Small prickles*—few. Color—Citron Yellow, Plate XVI Ridgway). *Hairs*—none.

*New shoots.*—*Color*—Warbler Green, Plate IV (Ridgway). *Large prickles*—several; medium length; hooked slightly downward; with medium-length narrow base. Color—Acajou Red, Plate XIII (Ridgway), tipped with Uranium Green, Plate 63/2, page 63. *Small prickles*—none to few. Color—Acajou Red, Plate XIII (Ridgway), tipped with Uranium Green, Plate 63/2, page 63. *Hairs*—none.

I claim:

A new and distinct variety of rose plant, as described and illustrated herein.

HERBERT C. SWIM.

No references cited.